US006916663B2

(12) United States Patent
Choi

(10) Patent No.: US 6,916,663 B2
(45) Date of Patent: Jul. 12, 2005

(54) DETECTION METHOD OF PROTEINS ON POLYACRYLAMIDE GELS USING A DYE COMPOSITION AS A SILVER ION SENSITIZING AGENT AND THE DYE COMPOSITION FOR THE SAME

(75) Inventor: Jung-Kap Choi, Kwangju (KR)

(73) Assignees: EZ Biopaq Co., Ltd. (KR); San-Ock Jeong (KR)

( * ) Notice: Subject to any disclaimer, the term of this patent is extended or adjusted under 35 U.S.C. 154(b) by 467 days.

(21) Appl. No.: 10/269,188

(22) Filed: Oct. 11, 2002

(65) Prior Publication Data

US 2004/0023401 A1 Feb. 5, 2004

(30) Foreign Application Priority Data

Aug. 1, 2002 (KR) ........................................ 2002-45612

(51) Int. Cl.[7] .......................... C09B 67/00; G01N 33/00

(52) U.S. Cl. .......................... 436/86; 436/88; 436/164; 436/166; 436/169; 436/174; 8/636; 8/657; 8/658

(58) Field of Search ........................... 436/86, 88, 164, 436/166, 169, 174; 8/636, 657, 658

(56) References Cited

U.S. PATENT DOCUMENTS 6,277,643 B1 * 8/2001 Choi et al. .................... 436/86

OTHER PUBLICATIONS

A. Andrews; *Electrophoresis*, Oxford University Press, New York, 2nd ed., pp. 1–58 (1988).

P. Wirth et al., *J. Chromatogr. A*, 698:123–143 (1995).

T. Rabilloud, *Electrophoresis*, 13:429–439 (1992).

J. Dzandu et al., *Analytical Biochemistry*, 174:157–167 (1988).

Z. Marczenko, Separation and Spectrophotometric Determination of Elements, p. 355(1986).

H. Flaschka et al., *J. Physiol. Chem.*, 289:279 (1952).

Prento et al., *Analyst*, 106:227–230 (1981).

Esfahan, *Fresenius' Journal of Analytical Chemistr*, 363(4):376–379 (1999).

V. Neuhoff et al., *Electrophoresis*, 6:427–448 (1985).

Compton et al., *Anal. Biochem.*, 151:369–374 (1985).

Heukeshoven et al., *Electrophoresis*, 6(3):103–112 (1985).

* cited by examiner

*Primary Examiner*—Monique T. Cole
(74) *Attorney, Agent, or Firm*—Peter F. Corless; Christine C. O'Day; Edwards & Angell, LLP

(57) ABSTRACT

The present invention relates to a method for detecting proteins on polyacrylamide gels, comprising the steps of sensitizing the proteins with a dye composition comprising an acidic organic dye as a silver ion sensitizing agent, and optionally, a basic organic dye as an auxiliary agent, and washing them, and then silver staining complexes of the protein-dye, and to the dye composition for the same.

8 Claims, 8 Drawing Sheets pH 4 pH 7

DETECTION METHOD OF PROTEINS ON POLYACRYLAMIDE GELS USING A DYE COMPOSITION AS A SILVER ION SENSITIZING AGENT AND THE DYE COMPOSITION FOR THE SAME

TECHNICAL FIELD

The present invention relates to a method for detecting proteins on polyacrylamide gels by silver staining, which uses a dye composition as a silver ion sensitizing agent, and to the dye composition for the same. More specifically, it relates to the method comprising the step of silver staining of proteins using the dye composition containing an acidic organic dye as the silver ion sensitizing agent, and optionally, a basic organic dye as an auxiliary agent without using glutaraldehyde that enables the rapid and easy detection of proteins with high sensitivity, and to the dye composition for the same.

BACKGROUND ART

Polyacrylamide Gel Electrophoresis (PAGE) is a protein analysis tool, extremely useful for separation, identification, purity verification, and size determination of proteins. Particularly, SDS-PAGE (Sodium Dodecyl Sulfate-PAGE) is a method wherein a protein is strongly bound to an anionic surfactant, i.e. SDS, at the ratio of 1.4:1 to have (−) charge on the surface, and so only its size acts as a separation factor. This method is widely used for protein analysis because it can be easily handled and has a good resolution rate (A. T. Andrews, *Electrophoresis*, 1–58).

Since most proteins that are subjects of analysis are colorless, and so an appropriate means is required for their detection. Therefore, various detection methods, e.g. organic dye staining method, silver staining method, fluorescence staining method, background staining method, etc., have been reported hitherto.

Organic dye staining method detects proteins by staining protein bands with an organic dye, e.g. Amido Black 10B, Ponceaus S, Fast Green FCF, Coomassie Brilliant Blue R (CBBR), etc. [*J. of Chromatography A*, 698, 123–143 (1995)]. Particularly, since the CBBR staining method is relatively simple and cost-effective, it has been generally used. However, the CBBR method has the problems that it takes a long time (4 to 6 hours) for staining and destaining, and does not have such good sensitivity [50 ng for Bovine Serum Albumin (BSA)].

Silver staining method, which has the highest sensitivity among non-radiological detection methods, is a method to impregnate and reduce silver ions [*J. of Chromatography A*, 698, 123–143 (1995)]. This method has very high sensitivity, capable of detecting proteins of 0.1 ng, but has such problems as the handling is complicated and the process is multi-step. It can be classified into silver nitrate method and diamine silver method depending on how to impregnate and reduce silver ions. Generally, the diamine silver method has good sensitivity, but requires complicated steps, and so the silver nitrate method is more widely used. However, in the silver nitrate method, an oxidizing agent like dichromate, or a reducing agent like glutaraldehyde or DTT must be used to overcome its low sensitivity and high background. Employment of such substances improves detection sensitivity, but may cause protein modifications or be harmful to a handler [*Electrophoresis* 13, 429–439 (1992)].

On the other hand, fluorescence staining method detects proteins by labeling the proteins with a fluorescent dye. This method has high detection sensitivity, but has the drawbacks to require UV irradiation and accurate quantitative instrumentation, and thereby to increase costs.

Background staining method, applicable only to an SDS-containing gel, detects proteins by forming precipitates with a metal salt on the gel surface excluding protein bands. This method can detect proteins within a short period of time, and so its utility is great. However, it also has a problem that storing the stained gel is difficult because the resulting band is not persistent [*Anal. Biochem.* 174, 157–167 (1988)].

Therefore, there has been a need to develop a new method for detecting proteins on polyacrylamide gels, which can rapidly and easily detect the proteins with high sensitivity as compared with the known staining methods.

DISCLOSURE OF THE INVENTION

To establish an improved silver staining method that can solve the above problems of the previous detection methods of proteins by the known silver staining, and that has enhanced sensitivity, the present inventors contemplated a "silver staining method using a dye as a silver sensitizing agent", wherein a dye composition comprising an acidic organic dye, and optionally, a basic organic dye is used as the silver ion sensitizing agent. That is, the present inventors found out that the detection sensitivity could be increased by 2–4 times through replacing the silver ion sensitizing agent, glutaraldehyde, for the known silver nitrate staining with the acidic organic dye. Furthermore, it was found that the acidic organic dye, if used in combination with the basic organic dye as an auxiliary agent, can shorten its staining and destaining time to facilitate its silver ion sensitizing function. Thus, the present invention was completed.

Therefore, an object of the present invention is to provide a method that can rapidly and easily detect proteins with high sensitivity under macroscopic observation through the whole staining procedures.

Another object of the present invention is to provide a dye composition as a silver ion sensitizing agent for use in the above method.

The first aspect of the present invention relates to a method for detecting proteins on polyacrylamide gels comprising the steps of:

(a) staining (sensitizing) the proteins with a dye composition containing an acidic organic dye as a silver ion sensitizing agent, and then, destaining (washing) them;

(b) impregnating silver ions to complexes of the protein-dye, and then, reducing them to metallic silver; and (c) observing the protein-dye-metallic silver complexes.

The second aspect of the present invention relates to a dye composition for detection of proteins on polyacrylamide gels by silver staining, containing an acidic organic dye as a silver ion sensitizing agent.

The examples of the acidic organic dye that can be used in the present invention include calcon dye derivatives (e.g. eriochrome black T, eriochrome blue black, solochrome black 6BN, eriochrome fast grey RAS or calcon carboxylic acid), alizarin yellow GG, alizarin yellow R, zincon, Bordeaux R, tryphan blue, or acid blue 92, and particularly, eriochrome black T, calcon carboxylic acid, or zincon. Preferable is eriochrome black T or calcon carboxylic acid, and more preferable is eriochrome black T. In addition, mixtures of two or more above acidic organic dyes, for example, a mixture of eriochrome black T and zincon, may be used in the present invention.

The dye composition according to the present invention may further contain a basic organic dye as an auxiliary agent. The examples of the basic organic dye include brilliant cresyl blue ALD, direct blue 71, crystal violet, methyl violet B base, methyl violet 10B, methyl violet B, ethyl green, rhodamine B, ethyl violet, phenosafranine or methylene blue, and particularly, brilliant cresyl blue ALD or ethyl violet.

Accordingly, the dye composition of the present invention may contain, i) eriochrome black T and brilliant cresyl blue ALD, ii) calcon carboxylic acid and ethyl violet, iii) zincon and ethyl violet, or iv) eriochrome black T, zincon, and ethyl violet, and preferably, i) eriochrome black T and brilliant cresyl blue ALD or ii) calcon carboxylic acid and ethyl violet, and more preferably, i) eriochrome black T and brilliant cresyl blue ALD. The dye composition of the present invention preferably contains i) eriochrome black T and brilliant cresyl blue ALD, ii) calcon carboxylic acid and ethyl violet, or iii) zincon and ethyl violet at themolar ratio of 1:0.1–1.5, or iii) eriochrome black T, zincon, and ethyl violet at the molar ratio of 0.1–1:1:0.1–1.5. Also, the composition may contain 3–10 v/v % acetic acid-containing acidic 20–40 v/v % ethanol aqueous solution or 3–10 v/v % acetic acid-containing acidic 20–50 v/v % methanol aqueous solution.

Hereinafter, the present invention will be explained in detail.

The dye-silver staining method of the present invention uses an acidic organic dye as a silver ion sensitizing agent and a basic organic dye as an auxiliary agent for counter ion effect. That is, the basic organic dye acts as the counter ion to the acidic organic dye to form ion-pairs, thereby to prevent staining of gels excluding proteins, and so shorten the subsequent destaining step.

In the present invention, azo dyes having polycyclic aromatic sulfonic acid group should be used as the acidic organic dye (silver ion sensitizing agent). The examples of the acidic organic dye for the present invention include eriochrome black T of the following formula 1, zincon of the following formula 2, and calcon carboxylic acid of the following formula 3:

Formula 1

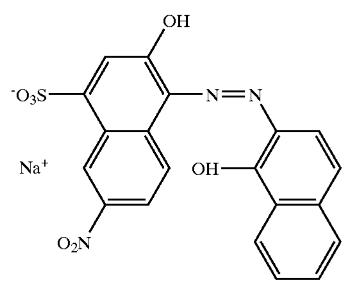

Formula 2

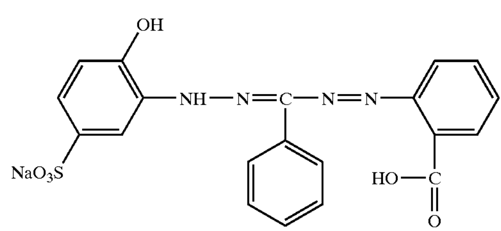

-continued

Formula 3

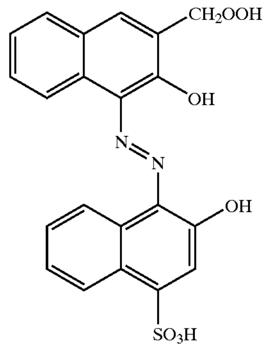

Eriochrome black T of the above formula 1 is used as 0.02% methanol solution for quantitation of Mg, Al, Be, Ca, Ga, In, lantanides, Th, Zn, etc. and known as an indicator for titration of EDTA [Z. Marczenko, Separation and Spectrophotometric Determination of Elements, 355 (1986)]. This dye contains sulfonic acid, diazo, nitro, and hydroxyl groups, and so is classified as an acidic dye. Its protein-staining effect varies to some extent depending on properties of solution and kinds of solvent, and so an excellent staining effect can be obtained in an acetic acid-containing mixed solvent of methanol or ethanol and water having pH 2 to 4.

Zincon of the formula 2 is one of O-hydroxyazo compounds, and is known as a metal chelating agent. It is a metal indicator to form a chelate compound with Zn, Cu, Hg, etc., and turns from red to blue under an alkaline condition of pH 8–10 [H. Flaschka and Huditz, *J. Physiol. Chem.*, 289, 279 (1952)]. This dye also contains sulfonic acid, diazo, carboxyl and hydroxyl groups, and so is classified as an acidic dye. Its protein-staining effect varies to some extent depending on properties of solution and kinds of solvent, and an excellent staining effect can be obtained in an acetic acid-containing mixed solvent of methanol or ethanol and water having pH 2 to 4. In the present invention, these two or more acidic organic dyes may be used together. The acidic organic dye binds to proteins and promotes nucleation and reduction of silver ions to improve sensitivity of silver staining. The dye is degraded and spontaneously decolorized during this procedure.

Calcon carboxylic acid of the formula 3, that is, 3-hydroxy-4-[(2-hydroxy-4-1-naphthalenyl)azo]-2-naphtahlene carboxylic acid is also called as Calred, Kalces, or Patton and Reeder's dye. It has been used as an indicator for the determination of microgram amounts of calcium in small biological samples by EDTA titration [Analyst (London) 106, 227–230 (1981)]. This dye also contains sulfonic acid, diazo, carboxyl, and hydroxyl groups, and so is classified as an acidic dye. Its protein-staining effect varies to some extent depending on properties of solution and kinds of solvent, and an excellent staining effect can be obtained in an acetic acid-containing mixed solvent of methanol or ethanol and water having pH 2 to 4.

Furthermore, a basic organic dye may be used as an auxiliary agent to promote staining by the acidic organic dye (silver ion sensitizing agent) in the present invention. The examples of the basic organic dye as the auxiliary agent include brilliant cresyl blue ALD of the following formula 4 or ethyl violet of the following formula 5:

Formula 4

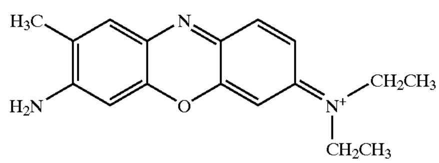

$Cl^- \cdot 1/2ZnCl_2$

Formula 5

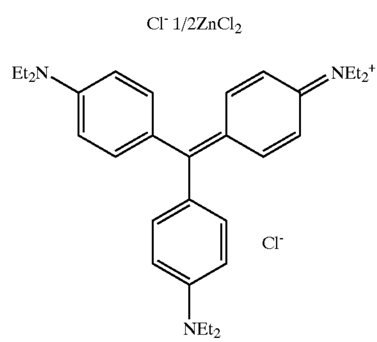

Brilliant cresyl blue ALD of the above formula 4, used together with eriochrome black T, is an acid-base indicator [Fresenius' J. of Analytical Chemistry 363, 376–379 (1999)] classified as a basic dye and used in quantitation of formaldehyde. Brilliant cresyl blue ALD alone stains proteins pale blue in a solvent having the same condition as that for eriochrome black T. However, brilliant cresyl blue ALD, combined with eriochrome black T, allows the eriochrome black T to selectively stain proteins to give an excellent synergistic silver ion-sensitizing effect.

Furthermore, ethyl violet of the above formula 5, used together with calcon carboxylic acid or zincon, is classified as a triarylmethane basic dye. It is used for quantitation of Pb or Cu, and is an acid-base indicator [*Analyst* (London), 112, 1011 (1987)]. Ethyl violet alone stains proteins pale blue in a solvent having the same condition as that for zincon. However, ethyl violet, combined with calcon carboxylic acid or zincon, allows the calcon carboxylic acid or zincon to selectively stain proteins to give an excellent synergistic silver ion-sensitizing effect.

In the present invention, it is important to appropriately pair two dyes having affinity each other. Preferable examples thereof are i) eriochrome black T and brilliant cresyl blue ALD, ii), calcon carboxylic acid and ethyl violet or iii) zincon and ethyl violet. In addition, two or more acidic organic dyes may be used together with a basic organic dye, for example, eriochrome black T and zincon as the acidic organic dye may be used together with ethyl violet as the basic organic dye.

In the present invention, eriochrome black T and/or zincon, or calcon carboxylic acid, together with brilliant cresyl blue ALD or ethyl violet, were applied to silver staining of proteins on polyacrylamide gels as a silver ion sensitizing agent. As a result, the acidic organic dye (silver ion sensitizing agent) was selectively bound to the proteins at a high speed and the destaining step was shortened to facilitate the silver staining. That is, eriochrome black T and/or zincon, or calcon carboxylic acid were added as the silver ion sensitizing agent, and brilliant cresyl blue ALD or ethyl violet was added at a relatively low concentration as an auxiliary agent to form ion pairs, thereby to minimize the penetration of eriochrome black T and/or zincon, or calcon carboxylic acid into background gels, and to increase staining intensity onto the protein bands, thereby to enhance the silver ion-sensitizing effect.

Table 1 shows acidic and basic organic dyes, which can be used in the present invention and their replaceable dyes, all of which fall within the scope of the present invention.

TABLE 1

| Silver ion sensitizing agent (dyes) | Dye (C.I. number) | Replaceable dye (C.I. number) |
|---|---|---|
| Eriochrome black T + Brilliant cresyl blue ALD | Eriochrome black T (14645) | Calcon dye derivatives |
| | | Eriochrome blue black (15705) |
| | | Solochrome black 6BN (14640) |
| | | Eriochrome fast grey RAS (15690) |
| | | Alizarin yellow GG (14025) |
| | | Alizarin yellow R (14030) |
| | Brilliant cresyl blue ALD | Direct blue 71 |
| | | Crystal violet (42555) |
| | | Methyl violet B base (42535B) |
| | | Methyl violet 10B (42555) |
| | | Methyl violet B (42535) |
| | | Ethyl green |
| | | Ethyl violet (42600) |
| | | Rhodamine B (45170) |
| Zincon + Ethyl violet | Zincon | |
| | Ethyl violet (42600) | Crystal violet (42555) |
| | | Methyl violet B base (42535B) |
| | | Methyl violet 10B (42555) |
| | | Methyl violet B (42535) |
| | | Ethyl green |
| Calcon carboxylic acid + Ethyl violet | Calcon carboxylic acid | Bordeaux R |
| | | Tryphan blue |
| | | Acid blue 92 (13390) |
| | Ethyl violet (42600) | Crystal violet (42555) |
| | | Methyl violet B base (42535B) |
| | | Methyl violet 10B (42555) |
| | | Methyl violet B (42535) |
| | | Ethyl green |
| | | Phenosafranine |
| | | Methylene blue |
| | | Rhodamine B (45170) |

The dye composition of the present invention is prepared by adding an acidic organic dye alone or in admixture with a basic organic dye in a solvent of acetic acid-containing acidic ethanol or methanol aqueous solution. In the preparation of the mixed dye composition, the acidic and basic organic dyes tend to form ion pairs and form precipitates, and so it is preferable to be prepared just before the use.

Moreover, a particle size of dye is very important for the dye-silver staining method according to the present invention, and it is preferable to maintain fine ion pairs (*Electrophoresis* 1985, 6, 427–448). The factors affecting the particle size of dye are concentration and mixing ratio of dyes, kind and ratio of alcoholic solvent, concentration of hydrogen ion, etc.

Considering all the above-described aspects, a preferable concentration of eriochrome black T is in the range of 0.0005 to 0.05 w/v %, and the most preferable is 0.005 w/v %. This is because its staining effect on protein bands is not good enough at the concentration less than 0.0005 w/v %, and the intensity difference between protein bands and background is decreased at the concentration more than 0.05 w/v %. A preferable concentration of zincon is in the range of 0.001 to 0.05 w/v %, and the most preferable is 0.004 w/v %. This is because its staining effect on protein bands is not good enough at the concentration less than 0.0001 w/v %, and the intensity difference between protein bands and background is decreased at the concentration more than 0.05 w/v %. Such facts can be confirmed from FIGS. 1*a* and 1*b* showing the intensities of stained protein bands depending on the concentration of eriochrome black T or zincon. Acidic organic dyes other than ernochrome black T or zincon, for example, calcon carboxylic acid, show similar staining intensity patterns depending on their concentrations to eriochrome black T or zincon.

A mixing ratio of acidic and basic organic dyes may be changed depending on their properties. It is preferable to mix them at an appropriate ratio in order to maximize effects of the dye-silver staining method without forming excessive precipitates as a result of experiments (see the following Table 2). Particularly, the above dye composition preferably contains eriochrome black T and brilliant cresyl blue ALD, calcon carboxylic acid and ethyl violet, or zincon and ethyl violet at the molar ratio of 1:0.1–1.5, or eriochrome black T, zincon, and ethyl violet at the molar ratio of 0.1–1:1:0.1–1.5. Also, it preferably contains 7 v/v % acetic acid-containing acidic 40 v/v % or 25 v/v % ethanol or 7 v/v % acetic acid-containing acidic 25 v/v % ethanol aqueous solution as a solvent. This is because under the above condition can be formed a particle size suppressing penetration of the dye (silver ion sensitizing agent) into the background gel without hampering its binding to the protein, thereby efficiently staining (sensitizing) the protein band.

For example, the dye-silver staining method according to the present invention may be practiced as follows. First, a gel separated after electrophoresis is washed and immobilized with 10 v/v % acetic acid-containing acidic 40 v/v % ethanol or methanol aqueous solution by shaking for 30 minutes or more. Then, it is stained (sensitized) with a dye composition by shaking with a shaker for about 5 to 60 minutes. The dye composition is prepared by dissolving acidic and basic organic dyes in 7 v/v % acetic acid-containing acidic 20–40 v/v % ethanol or 20–50 v/v % methanol aqueous solution just before its use. The stained gel is subjected to removal of the silver ion sensitizing agent in a destaining solution (3–10 v/v % acetic acid-containing acidic 20–40 v/v/% ethanol or 20–50 v/v % methanol aqueous solution) for 5 to 30 minutes, and subsequently, in water for about 5 to 30 minutes. The staining and destaining time is suitably adjusted depending on kinds of the used dye. The destained gel is silver stained by the known silver nitrate method. Composition of dye, required time, staining and destaining solution, and sensitivity are as shown in the following Table 2.

TABLE 2

| Dye | Final conc. (Optimal conc.) (w/v %) | Time (min) Washing/ Immob. | Staining | Destaining (EtOH sol'n/water) | Staining sol'n $CH_3COOH$/EtOH/water | Destaining sol'n $CH_3COOH$/EtOH/water | Sensitivity (ng) |
|---|---|---|---|---|---|---|---|
| EBT | 0.0005–0.05 (0.005) | 30–60 | 5–10 | 10 × 2/15 | 7/40/53 | 10/30/60 | 0.04–0.1 |
| BCB | 0.0005–0.05 (0.001) | | | | | | |
| Zincon | 0.001–0.05 (0.004) | 30–60 | 5–10 | 10 × 2/15 | 7/25/68 | 3/24/73 | 0.04–0.1 |
| EV | 0.001–0.05 (0.003) | | | | | | |
| CCA | 0.001–0.05 (0.01) | 30–60 | 5–10 | 10 × 2/15 | 7/40/53 | 7/30/63 | 0.04–0.1 |
| EV | 0.0005–0.05 (0.003) | | | | | | |
| EBT | 0.0005–0.05 (0.0006) | 30–60 | 5–10 | 10 × 2/15 | 7/25/68 | 3/24/73 | 0.04–0.1 |
| Zincon | 0.001–0.05 (0.004) | | | | | | |
| EV | 0.001–0.05 (0.003) | | | | | | |

EBT: Eriochrome Black T
BCB: Brilliant Cresyl Blue
EV: Ethyl Violet
CCA: Calcon Carboxylic Acid
(Conc.: Concentration; Immob.: Immobilization, Sol'n: Solution)

The almost same result as in the above Table 2 can be also obtained when using an acidic organic dye alone as a silver sensitizing agent or a methanol solution as staining and destaining solution. However, the staining and destaining may be delayed with using the acidic organic dye alone, or there may be a toxicity problem when using the methanol solution.

BEST MODE FOR CARRYING OUT THE INVENTION

Figure 1A:
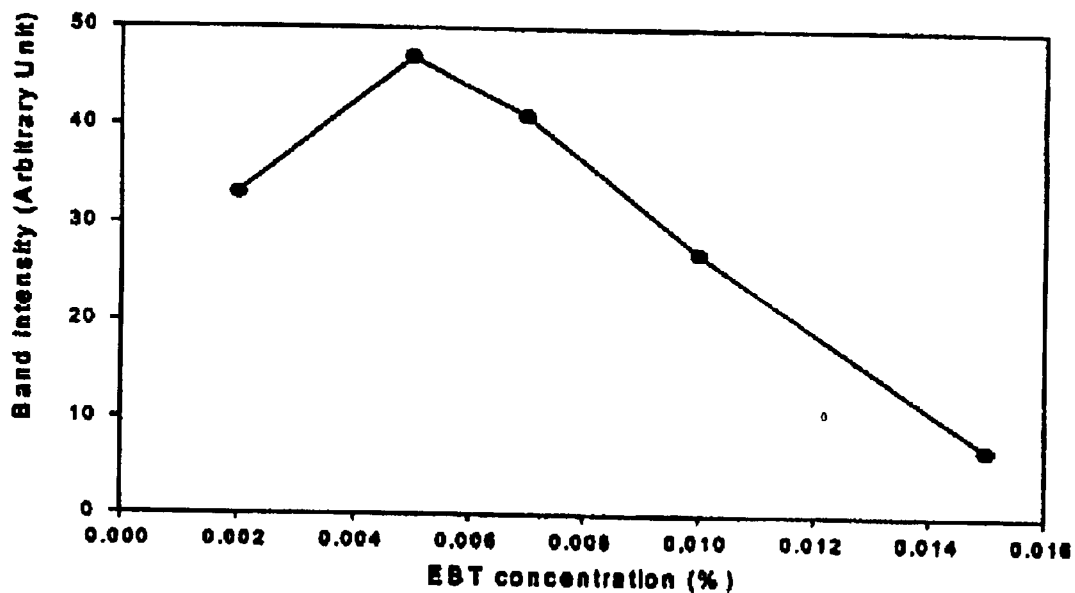
FIGS. 1*a* to 1*c* are graphs showing staining intensities of the protein bands depending on concentrations of eriochrome black T (a), zincon (b), and calcon carboxylic acid (c) treated after electrophoresis.
Figure 1B:
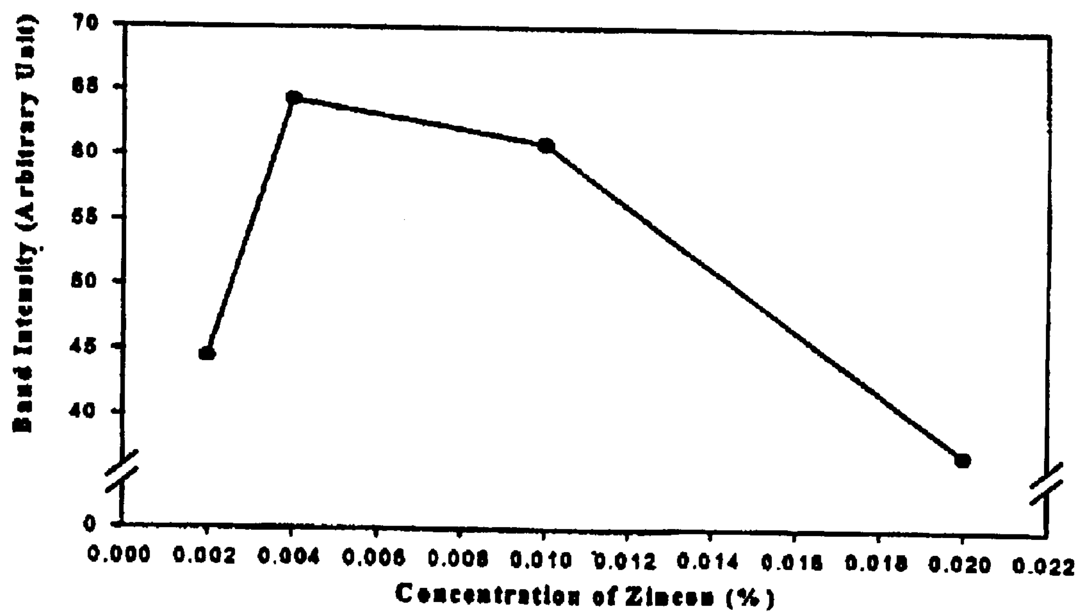
Figure 1C:
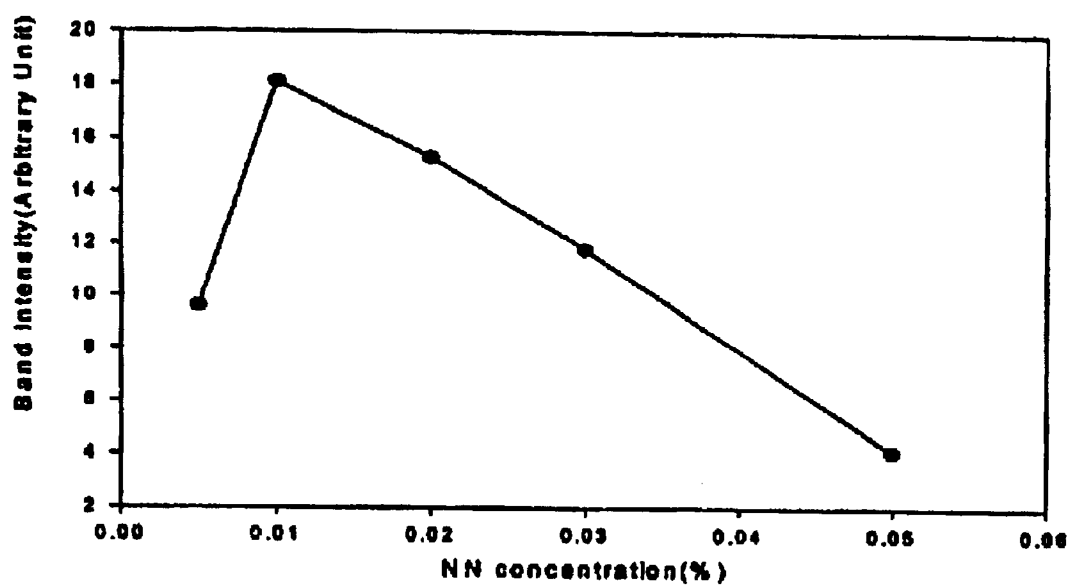

The present invention will be more specifically illustrated by the following examples. However, the following examples should not be construed as limiting the scope of the present invention.

EXAMPLES 1 TO 4

(1) Preparation of Gel and Electrophoresis

An SDS-containing slab gel was prepared according to the Laemmli's method. A concentration of protein was determined by Bradford method (*Anal. Biochem.* 151, 369–374) using Standard I for the quantitation of protein (Bio-Rad Corp.). Before performing electrophoresis, protein standards, myosin (205 kDa), β-galactosidase (116 kDa), phosphorylase b (97.4 kDa), BSA (66 kDa), ovalbumin (45 kDa), and carbonic anhydrase (29 kDa), were mixed at the same amount as a protein sample, and the above mixture was heated to 100° C. in a sample buffer solution (70 mM Tris-HCl, pH 6.8, 11.4% glycerol, 3% SDS, 0.01% bromophenol blue, β-mercaptoethanol) for 5 minutes. The solution was loaded onto wells at concentrations of 10, 5, 2.5, 1.2, 0.6, 0.3, 0.15, 0.08, 0.04 and 0.02 ng per protein band in order from the left well. A developing buffer solution was the solution containing 0.025 M Tris, 0.2 M glycine, and 0.1% SDS, the pH of which was 8.3. The gel had the thickness of 1 mm. A stacking gel (4.5%) with the length of 1.5 cm was stacked on a separating gel (10%) (acrylamide:bisacrylamide=30:0.8). Then, electrophoresis was performed using Mini-protein II slab gel apparatus at a fixed electric current of 22 mA for 60 minutes.

(2) Silver Staining

To increase the silver sensitizing effect of the dye by removing interfering substances such as a buffer solution, SDS, etc, the separated gel after electrophoresis was washed and immobilized in 10 v/v % acetic acid-acidic 40 v/v % ethanol solution while shaking it for 30 minutes or more. Each staining and destaining time was controlled as shown in the following Table 3 depending on kinds of the used dye (silver ion sensitizing agent). The gel was stained with the dye composition as shown in the following Table 3 with shaking it with a shaker for about 5 or 10 minutes. The above dye composition was prepared by dissolving acidic and basic organic dyes in 7 v/v % acetic acid-containing acidic 25 v/v % or 40 v/v % ethanol aqueous solution just before the use. Upon completion of the staining, the gel was subjected to removal of residual silver ion sensitizing agent twice in the destaining solution for 10 minutes each time, and subsequently, in water for 15 minutes. The destained gel was silver stained according to the known silver nitrate method. That is, the gel was immersed in 0.2% silver nitrate solution for 20 minutes to form complexes of the protein-silver ion sensitizing agent, and washed twice for 0.5–2 minutes, and the silver ions were reduced with 0.5–3% $Na_2CO_3$ solution with 0.01–0.05% HCHO and 0.0004–0.001% $Na_2S_2O_3$ to develop color. Upon completion of silver ion reduction, the gel was immersed in 1.5% EDTA for 10 minutes to stop the reduction reaction, and then, washed with water. It was transferred to a filter paper and dried on a gel drier at 65° C. for 40 minutes and stored. The results are shown in the following Table 3 and FIGS. 2*a* to 2*d*.

TABLE 3

| | | | Time (m) | | | | | |
|---|---|---|---|---|---|---|---|---|
| Ex. | Dye | Conc. of dye | Washing/ Immob. | Staining | Destaining (EtOH sol'n/water) | Staining sol'n $CH_3COOH$/EtOH/water | Destaining sol'n | Sensitivity (ng) |
| 1 | EBT | 0.005 | 60 | 5 | 10 × 2/15 | 7/40/53 | 10/30/60 | 0.04–0.1 |
| | BCB | 0.001 | | | | | | |
| 2 | Zincon | 0.004 | 60 | 10 | 10 × 2/15 | 7/25/68 | 3/24/73 | 0.04–0.1 |
| | EV | 0.003 | | | | | | |
| 3 | CCA | 0.01 | 60 | 5 | 10 × 2/15 | 7/40/53 | 7/30/63 | 0.04–0.1 |
| | EV | 0.003 | | | | | | |
| 4 | EBT | 0.0006 | 60 | 10 | 10 × 2/15 | 7/25/68 | 3/24/73 | 0.04–0.1 |
| | Zincon | 0.004 | | | | | | |
| | EV | 0.003 | | | | | | |

EBT: Eriochrome Black T
BCB: Brilliant Cresyl Blue
EV: Ethyl Violet
CCA: Calcon Carboxylic Acid
Conc.: Concentration; Immob.: Immobilization, Sol'n: Solution

EXAMPLES 5 TO 8

(1) Preparation of 2D Gel and Isoelectric Focusing (IEF)

For re-swelling an isoelectric focusing gel, an isoelectric focusing gel strip (7 cm, pH 4 to 7) manufactured by Pharmacia was immersed in a re-swelling buffer solution containing a sample for 12 hours to load the sample simultaneously with re-swelling the isoelectric focusing gel. The sample had a total volume of 125 μl by adding 8 μl of DTT and 114.2 μl of a re-hydration buffer solution to *E. Coli* BL21 (25 μg/2.8 μl). For electrophoresis of the isoelectric focusing gel, the above focusing gel was transferred to an IEF tray, and electrophoresis (gel focusing) was carried out with circulating cooling water for 4 hours. EPS 3501 XL power supply was used as the power for electrophoresis and an electric voltage was slowly increased as follows: 0 to 200 V for 2 minutes; 200 to 3500 V for 90 minutes; and 3500 V for 150 minutes. After performing the gel focusing as described above, 5 ml of an equilibrium buffer solution and 50 mg of DTT were added to the strip to reach the equilibrium for 15 minutes. Then, the focusing strip was loaded onto an SDS-PAGE gel (13%, 10×10 cm) together with protein standards. Electrophoresis was carried out using Hoefer Mighty Small electrophoretic apparatus at a fixed electric current of 22 mA for 60 minutes.

(2) Silver Staining of the 2D Gel

The same procedures as in the above Examples 1 to 4 were carried out except that the above 2D gel was used as a gel to stain. The results are shown in FIGS. 3*a* to 3*d*.

COMPARATIVE EXAMPLE 1

Figure 2A:
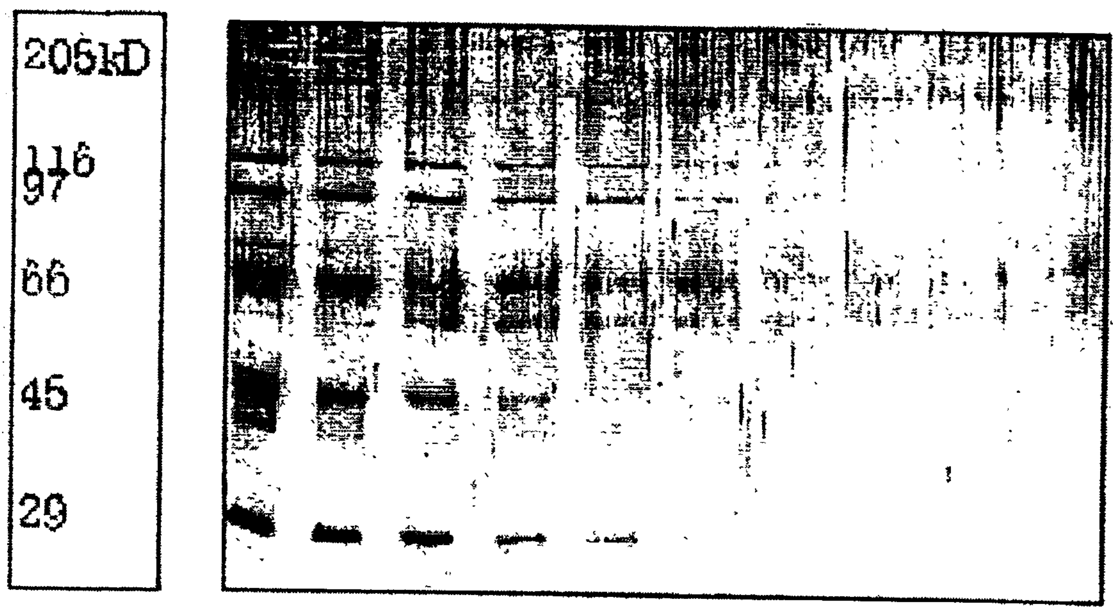
FIGS. 2*a* to 2*e* are photographs comparing the detection sensitivities and staining patterns for protein standards in SDS-polyacrylamide gels when using eriochrome black T and brilliant cresyl blue ALD (a); zincon and ethyl violet (b); calcon carboxylic acid and ethyl violet (c); and eriochrome black T, zincon, and ethyl violet (d) in acetic acid/ethanol staining solution, with those of silver nitrate staining method using glutaraldehyde (e), as a silver ion sensitizing agent.
Figure 2B:
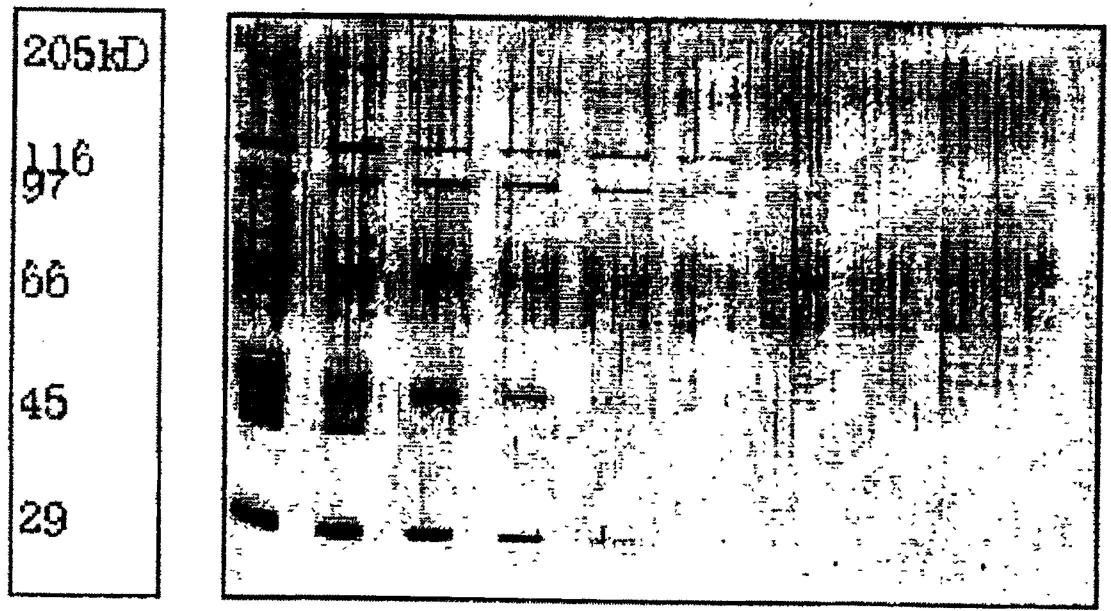
Figure 2C:
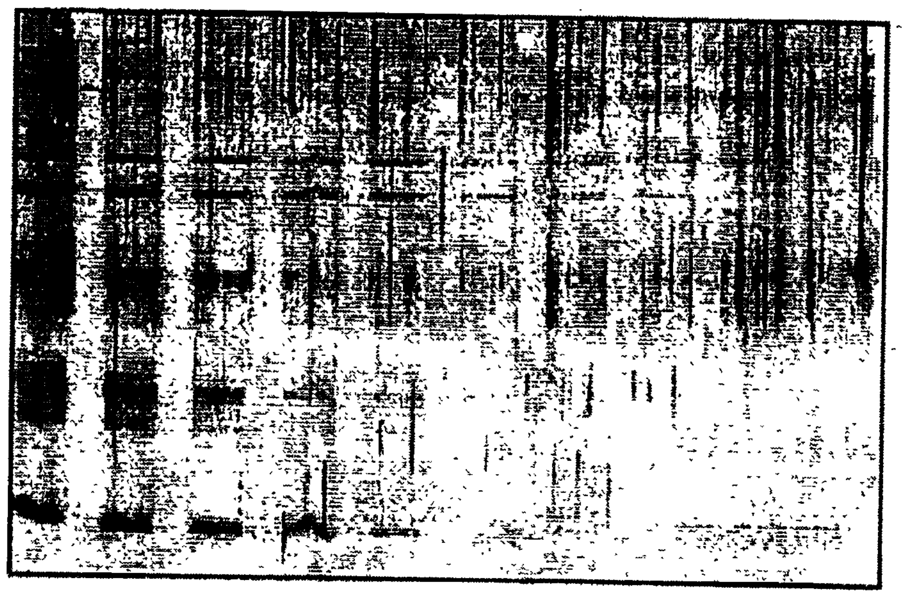
Figure 2D:
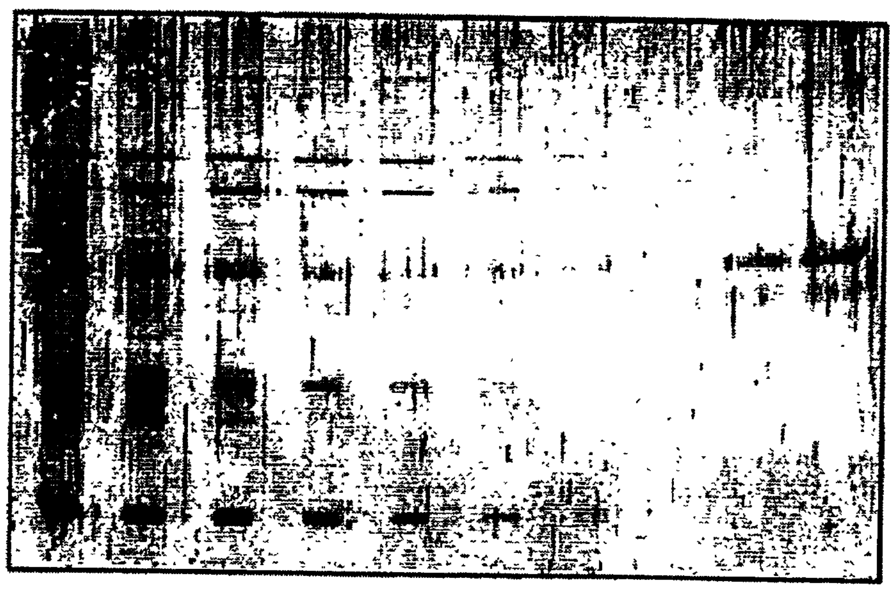
Figure 2E:
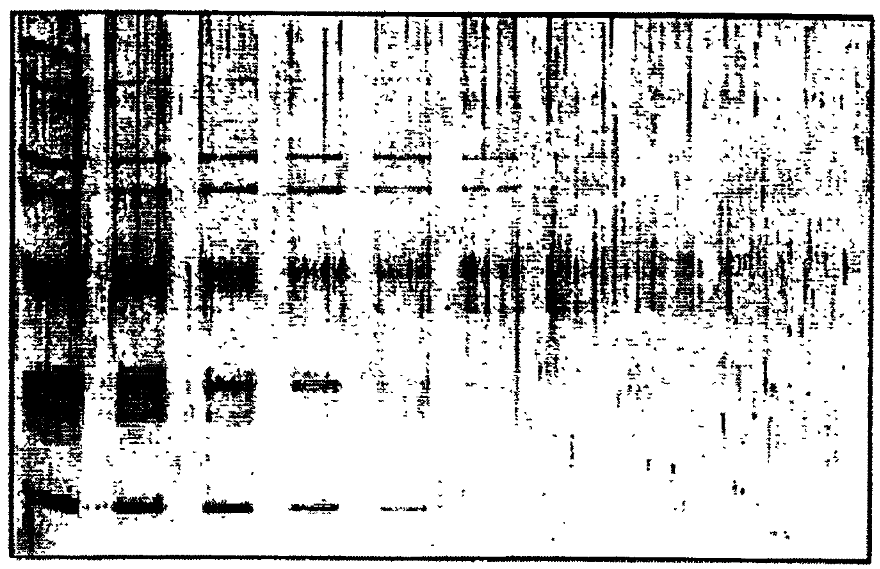

Silver nitrate staining was carried out by the Heukeshoven, et al.'s method [*Electrophoresis* 6, 103–112 (1985)]. The gel prepared in the same manner as in Examples 1 to 4 was immobilized. Subsequently, it was reacted in 6.8% $CH_3COONa$ solution with 0.125% glutaraldehyde and 0.2% $Na_2S_2O_3$ for 30 minutes, and then, washed with water three times for 5 minutes. The gel was silver stained in 0.015% formaldehyde aqueous solution with 0.25% silver nitrate, and then, washed with water twice for 1 minute. The silver ion was reduced and developed color with 3% $Na_2CO_3$ solution with 0.008% HCHO. Upon completion of silver ion reduction, the gel was immersed in 1.5% EDTA to stop the reduction reaction and washed with water. This was transferred to a filter paper, dried on 65° C. gel drier for 40 minutes and stored. The results are shown in FIG. 2*e*.

COMPARATIVE EXAMPLE 2

Figures 3A, 3B:
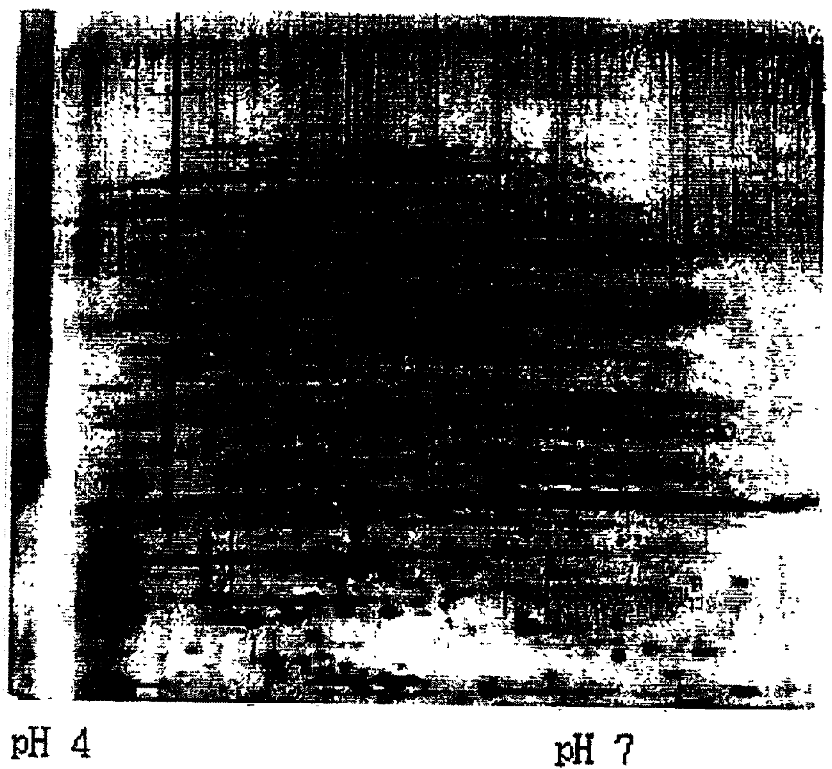
FIGS. 3*a* to 3*e* are photographs comparing detection sensitivities and staining patterns for protein standards in 2D SDS-polyacrylamide gels when using eriochrome black T and brilliant cresyl blue ALD (a); zincon and ethyl violet (b); calcon carboxylic lo acid and ethyl violet (c); and eriochrome black T, zincon, and ethyl violet (d) in acetic acid/ethanol staining solution, with those of silver nitrate staining method using glutaraldehyde (e), as a silver ion sensitizing agent.
Figure 3C:
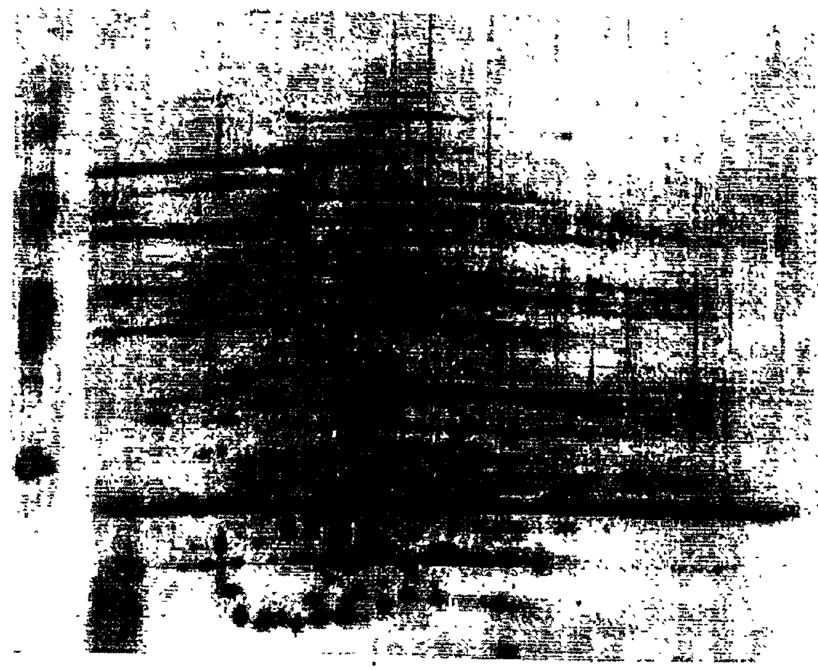
Figure 3D:
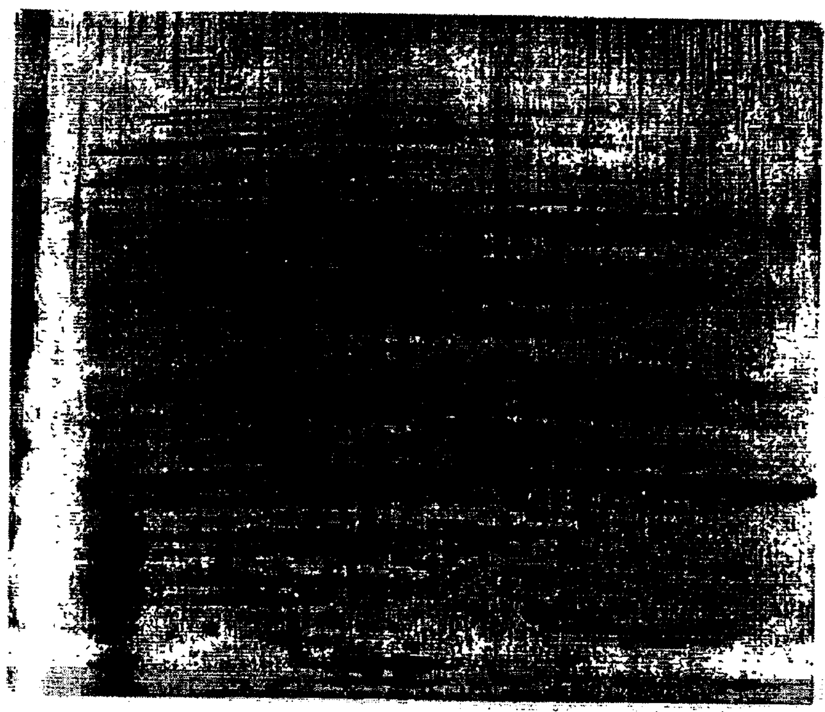
Figure 3E:
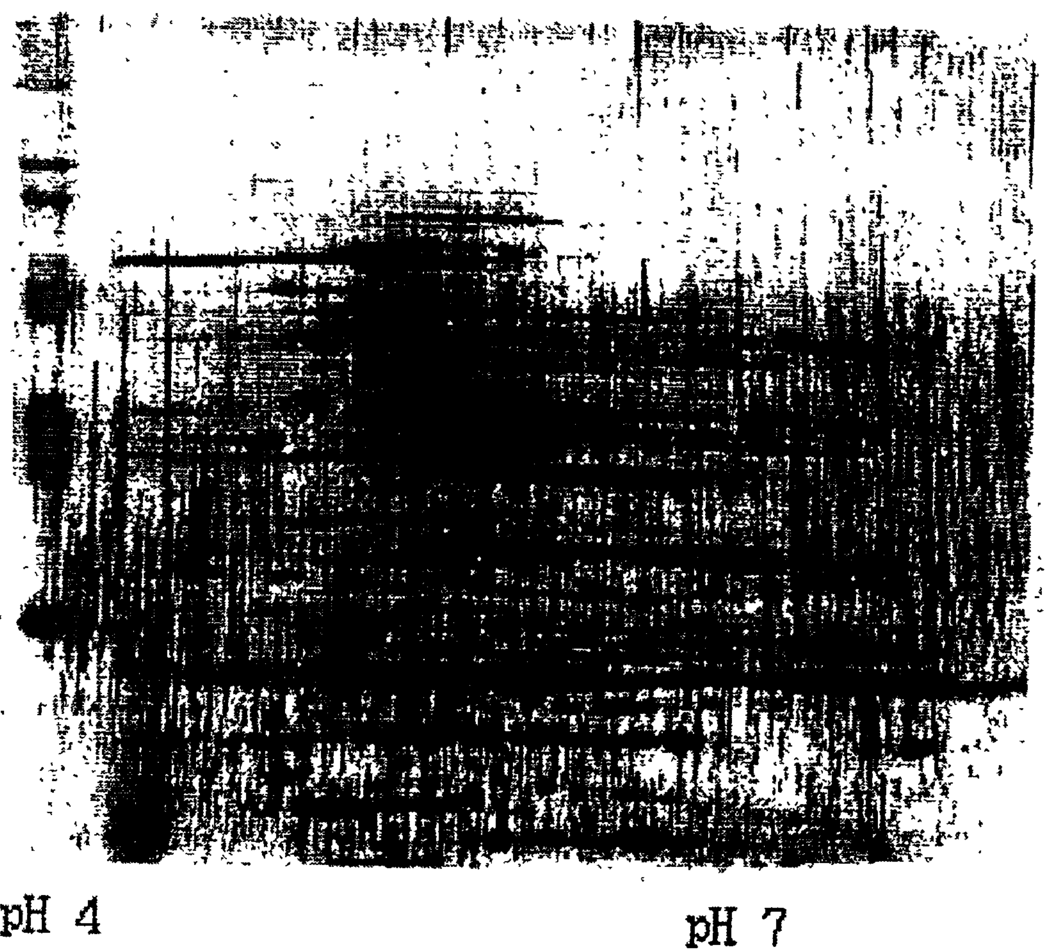

The 2D gel prepared in the same manner as in Examples 5 to 8 was stained according to the substantially same method as in Comparative Example 1. The results are shown in FIG. 3*e*.

It was confirmed from FIGS. 2*a* to 2*e* that the silver staining method using a dye composition as a silver ion sensitizing agent could visualize 0.04–0.08 ng or more of protein standards, such as myosin (205 kDa), β-galactosidase (116 kDa), phosphorylase b (97.4 kDa), BSA (66 kDa), ovalbumin (45 kDa), and carbonic anhydrase (29 kDa) (FIGS. 2*a* to 2*d*), while the known silver staining method, silver nitrate method using glutaraldehyde, could visualize 0.15 ng or more of the protein standards (FIG. 2*e*), and so the detection sensitivity of protein was increased by about 2–4 times. Further, it was confirmed from FIGS. 3*a* to 3*e* that the dye-silver staining method had the same staining pattern on the 2D gel, but had the improved sensitivity, as compared with the known silver staining method.

In conclusion, the present invention using an acidic organic dye alone as a silver ion sensitizing agent or in combination with a basic organic dye as an auxiliary agent minimizes staining of background gels and has the synergistic effect of silver nucleation and reduction by the acidic organic dye. Therefore, the detection limit of the prior silver staining method can be increased by 2–4 times without using harmful glutaraldehyde as a silver ion sensitizing agent. Furthermore, the whole staining process can be visualized to facilitate the silver staining method, and proteins on 2D gels can be also detected with improved sensitivity.

INDUSTRIAL APPLICABILITY

The present invention enables the rapid and easy detection of proteins on polyacrylamide gels without using glutaraldehyde to have 2- to 4-fold increased sensitivity, and further, can visualize protein bands during the whole staining process to facilitate the silver staining, and detect protein on 2D gels with improved sensitivity.

What is claimed is:

1. A method for detecting proteins on polyacrylamide gels, comprising the steps of:

(a) sensitizing the proteins with a dye composition to form a protein dye complex, containing one or more acidic organic dyes selected from the group consisting of calcon dye derivatives, alizarin yellow GG, alizarin yellow R, zincon, Bordeaux R, tryphan blue, and acid blue 92 as a silver ion sensitizing agent, and a basic organic dye selected from the group consisting of brilliant cresyl blue ALD, direct blue 71, crystal violet, methyl violet B base, methyl violet 10B, methyl violet B, ethyl green, rhodamine B, ethyl violet, phenosafranine and methylene blue as an auxiliary agent; and then, washing them;

(b) impregnating silver ions to complexes of the protein-dye, and then, reducing them to metallic silver; and (c) observing the protein-dye-metallic silver complexes.

2. The method of claim 1, wherein said calcon dye derivative is selected from the group consisting of eriochrome black T, eriochrome blue black, solochrome black 6BN, eriochrome fast grey RAS and caleon carboxylic acid.

3. The method of claim 2, wherein said acidic organic dye is one or more selected from the group consisting of eriochrome black T, zincon, and calcon carboxylic acid.

4. The method of claim 3, wherein eriochrome black T has a concentration in the range of 0.0005 to 0.05 w/v %, or calcon carboxylic acid or zincon has a concentration in the range of 0.001 to 0.05 w/v %.

5. The method of claim 1, wherein the basic organic dye is brilliant cresyl blue ALD or ethyl violet.

6. The method of claim 3, wherein the dye composition contains eriochrome black T and brilliant cresyl blue ALD; calcon carboxylic acid and ethyl violet; zincon and ethyl violet; or eriochrome black T, zincon, and ethyl violet.

7. The method of claim 6, wherein the dye composition contains eriochrome black T and brilliant cresyl blue ALD; calcon carboxylic acid and ethyl violet; or zincon and ethyl violet at the molar ratio of 1:0.1–1.5; or eriochrome black T, zincon, and ethyl violet at the molar ratio of 0.1–1:1:0.1–1.5.

8. The method of claim 1, wherein the dye composition contains 3–10 v/v % acetic acid-containing acidic 20–40 v/v % ethanol aqueous solution or 3–10 v/v % acetic acid-containing acidic 20–50 v/v % methanol aqueous solution as a solvent.

* * * * *